(12) United States Patent
Khunkitti et al.

(10) Patent No.: US 8,932,655 B2
(45) Date of Patent: Jan. 13, 2015

(54) ANTISEPTIC TEAT DIP MICROEMULSION

(75) Inventors: Watcharee Khunkitti, Thailand (TH); Chantana Aromdee, Thailand (TH); Mukda Chitcharoenthum, Thailand (TH); Netchanok Jiwakanon, Thailand (TH)

(73) Assignee: The Thailand Research Fund, Bangkok (TH)

( * ) Notice: Subject to any disclaimer, the term of this patent is extended or adjusted under 35 U.S.C. 154(b) by 256 days.

(21) Appl. No.: 12/735,965

(22) PCT Filed: Feb. 28, 2008

(86) PCT No.: PCT/SG2008/000066
§ 371 (c)(1),
(2), (4) Date: Dec. 7, 2010

(87) PCT Pub. No.: WO2009/108120
PCT Pub. Date: Sep. 3, 2009

(65) Prior Publication Data
US 2011/0086117 A1    Apr. 14, 2011

(51) Int. Cl.
| | |
|---|---|
| *A61K 36/899* | (2006.01) |
| *A61K 36/00* | (2006.01) |
| *A61K 36/889* | (2006.01) |
| *A61K 36/752* | (2006.01) |
| *A61K 36/48* | (2006.01) |
| *A61K 36/28* | (2006.01) |
| *A01N 25/00* | (2006.01) |
| *A01N 65/00* | (2009.01) |
| *A61K 9/08* | (2006.01) |
| *A61K 47/02* | (2006.01) |
| *A61K 47/10* | (2006.01) |
| *A61K 47/12* | (2006.01) |
| *A61K 47/20* | (2006.01) |
| *A61K 47/44* | (2006.01) |

(52) U.S. Cl.
CPC .............. *A61K 36/899* (2013.01); *A01N 65/00* (2013.01); *A61K 9/08* (2013.01); *A61K 47/02* (2013.01); *A61K 47/10* (2013.01); *A61K 47/12* (2013.01); *A61K 47/20* (2013.01); *A61K 47/44* (2013.01)
USPC ........... 424/750; 424/776; 424/727; 424/736; 424/757; 424/764; 424/405

(58) Field of Classification Search
None
See application file for complete search history.

(56) References Cited

U.S. PATENT DOCUMENTS 7,144,591 B2 * 12/2006 Bencsits ........................ 424/725
2007/0141127 A1 * 6/2007 Casas-Sanchez et al. .... 424/443

OTHER PUBLICATIONS

Bassole et al. (2011) Phytomedicine 18: pp. 1070-1074.*
Gbenou et al. (2013) Mol. Biol. Rep. 40: pp. 1127-1134.*
Hammer et al. (1999) J. Appl. Microbiol. 86: pp. 985-990.*
Hanaa et al. (2012) Annals Agric. Sci. 57(2): pp. 113-116.*
Masamba et al. (2003) Malawi J. Agric. Sci. 2(1): pp. 56-64.*
Pattnaik et al. (1997) Microbios 89: pp. 39-46.*
Prabuseenivasan et al. (2006) BMC Complementary and Alternative Medicine 6: 39.*
Wattiaux, M.A. Website document entitled 24) Mastitis: Prevention and Detection. (available at http://babcock.wisc.edu/node/218).*

* cited by examiner

*Primary Examiner* — Chris R Tate
*Assistant Examiner* — Russell Fiebig
(74) *Attorney, Agent, or Firm* — Axis Intellectual Capital Pte Ltd; Leif R. Sloan; Sonya C. Harris

(57) ABSTRACT

An aqueous antiseptic composition for eliminating microorganisms that cause Bovine mastitis in dairy animals is disclosed. The composition comprises about 10 to 50% by volume of lemongrass oil and at least one solubilizing agent for solubilizing the lemongrass oil. The composition also comprises about 10 to 30% by volume of a carrier oil carrying the components of the composition and about 0.5 to 2% by volume of an electrolyte for providing conductivity for the composition. The composition further comprises an organic acid for adjusting the pH level of the composition and an antioxidant.

9 Claims, No Drawings

ANTISEPTIC TEAT DIP MICROEMULSION

FIELD OF INVENTION

The invention generally relates to a composition for cleaning and disinfection, and more particularly, to prevent inflammation of the udder in dairy animals caused by bacterial infection.

BACKGROUND

Bovine mastitis is a condition where the udder of a dairy animal becomes infected and is caused by a broad spectrum of pathogenic microorganisms. Examples of such pathogenic microorganisms are *Staphylococcus aureus, Streptococcus agalactiae, Escherichia coli, Bacillus cereus* and *Candida albicans*.

If untreated, the condition usually leads to the inflammation of the udder. This typically results in an undesirable reduction in the quantity as well as the quality of milk produced by the dairy animal.

In order to effectively control and prevent the occurrence of bovine mastitis, the udder of the dairy animal is usually treated with an antiseptic lotion or disinfectant before and after the dairy animal is milked.

Conventional antiseptic lotions contain a variety of antimicrobial agents for eliminating the presence of pathogenic microorganisms found on the udder of dairy animals. These antimicrobial agents include chemicals such as iodophers, quantenary ammonium compounds, chlorhexidine salts, chlorine release compounds, oxidizing compounds, protonated carboxylic acids, acid anionics and chlorine dioxide. The chemicals found in the antimicrobial agents are undesirable for prolong use in disinfecting the udder of dairy animals.

Other conventional antiseptic lotions contain substances that are naturally produced and less toxic, such as essential oils. Essential oils are found naturally in plants and have antimicrobial properties. The oils are extracted through a distillation process and are usually hydrophobic. This means that the oils are not suitable for formulating into an aqueous mixture.

The United States of America Food and Drug Administration (FDA) classifies lemongrass as GRAS (Generally Recognized As Safe). This means experts consider lemongrass a safe substance when it is added to food. Lemongrass is therefore exempted from the Federal Food, Drug, and Cosmetic Act (FFDCA) food additive tolerance requirements.

Studies conducted by Brian et al., published in Journal of Agriculture Food Chemistry, 2002, Vol. 50, Pg 1345-1349, show that essential oil extracted from lemongrass processes antimicrobial properties. However, the essential oil of lemongrass is not readily soluble and therefore, is unsuitable for use in formulating into an aqueous mixture.

There is therefore a need to provide an essential oil that is hydrophilic for formulating into an aqueous mixture and for disinfecting the udder of dairy animals.

SUMMARY

Embodiments of the invention are disclosed hereinafter for an aqueous antiseptic composition for eliminating microorganisms that cause Bovine mastitis in dairy animals.

The aqueous antiseptic composition comprises about 10 to 50% by volume of lemongrass oil having antimicrobial properties and about 10 to 30% by weight of at least one solubilizing agent for solubilizing the lemongrass oil. The composition also comprises about 10 to 30% by volume of a carrier oil carrying the components of the composition and about 0.5 to 2% by volume of an electrolyte for providing conductivity for the composition. The composition further comprises an organic acid for adjusting the pH level of the composition and an antioxidant.

DETAILED DESCRIPTION

The composition of the present invention is an aqueous antiseptic composition of a predetermined concentration. The composition has antimicrobial properties and is used for eliminating microorganisms that cause Bovine mastitis in dairy animals.

In particular, there are five species of microorganisms that are known to cause Bovine mastitis in dairy animals. The five species of microorganisms are *Staphylococcus aureus, Streptococcus agalactiae, Escherichia coli, Pseudomonas aeruginosa* and *Bacillus cereus*.

The composition is capable of being used as an antiseptic for treating the udders of dairy animals to effectively control and prevent the occurrence of bovine mastitis. The composition comprises an essential oil, one or more solubilizing agent, an electrolyte, an antioxidant, a carrier oil and an organic acid. The antioxidant prevents oxidation of citral and other unsaturated hydrocarbon compounds.

The essential oil is preferably extracted from *Cymbopogon citratus* (DC) Stapf (Gramineae), which is commonly known as lemongrass. The essential oil of lemongrass is preferably obtained through steam distillation. The essential oil mainly comprises citral, which is a mixture of bioactive isomers neral, and geranial.

More specifically, through gas chromatography and mass spectroscopy (GC MS), the essential oil is found to comprise by volume 74.2% of citral, 9.82% of linalool, 5.99% of β-myrcene, 4.37% of geraniol, 2.17% of citronellal and 1.23% of geranyl acetate.

Table 1 shows the chemical constituents of the essential oil of lemongrass and the respective constituent's percentage by volume from GC MS.

TABLE 1

| Chemical constituents | Percentage (by volume) |
|---|---|
| linalool | 9.82 |
| 2-decyne-1-ol | 1.47 |
| citronellal | 2.17 |
| B-citral | 31.95 |
| geraniol | 4.37 |
| A-citral | 43.25 |
| geranyl acetate | 1.23 |
| unidentified | 5.74 |

The essential oil is also the primary component in the composition that has antimicrobial properties for eliminating the microorganisms that cause Bovine mastitis in dairy animals.

The composition preferably comprises about 10 to 50% by volume of the essential oil, and preferably, about 10 to 25% by volume of the essential oil as an active component of the composition.

Additionally, the composition comprises about 10 to 50% by volume of the carrier oil and preferably, about 10 to 25% by volume as an emollient. The carrier oil provides smoothing and moisturizing effects to the udder of dairy animals as well as prolonging the contact time of the composition with the udder. In another embodiment of the invention, the carrier oil preferably comprises a synthetic oil and a vegetable or natural oil.

Specific examples of the synthetic oil and the vegetable oil are mineral oil, isopropyl myristate oil, isopropyl palmitate oil, palm oil (*Elaeis guineensis*), sunflower oil (*Helianthus annus*), olive oil (*Olea europaea*), coconut oil (*Cocos nucifera*), sesame oil (*Sesamum idicum*) and soya bean oil (*Glycine max*). In an embodiment of the invention, the mineral oil and the olive oil are preferably used as the synthetic oil and the vegetable oil respectively.

Furthermore, the composition comprises one or more solubilizing agents. The solubilizing agents solubilize each of the essential oil and carrier oil. Examples of the solubilizing agents are polyethylene glycol 1000 monocetyl ether, polyoxethylene monolaurate, polyxyethylene, monolaurate, sodium lauryl sulfate, sodium-2-ethyhexyl sulfosuccinate and simethyl amine oxide.

The composition preferably comprises about 10 to 30% by weight of the solubilizing agents. The solubilizing agents preferably comprise polyethylene glycol 1000 monocetyl ether and sodium lauryl sulfate, in a proportion of 1:2.

Besides the essential oil and solubilizing agents, the composition further comprises an electrolyte. The electrolyte is for reducing evaporation of the essential oil. Examples of suitable electrolytes include sodium chloride and sodium citrate. The composition preferably comprises about 0.5 to 2% by weight of the electrolyte, for example 2% by weight of sodium chloride.

The pH level of the composition ranges from 3 to about 6. The pH level is adjustable with an organic acid. Examples of suitable organic acid are acetic acid, citric acid and tartaric acid. Citric acid is preferably used as the organic acid for adjusting the pH level of the composition.

The composition is capable of effectively eliminating microorganisms that cause Bovine mastitis in dairy animals. Table 2 shows the antimicrobial efficacy of the composition on the microorganisms.

TABLE 2

| Microorganisms | Contact time (sec) | |
|---|---|---|
| | 1-log reduction | 3-log reduction |
| *Staphylococcus aureus* | 1.62 | 4.87 |
| *Streptococcus agalactiae* | 1.73 | 5.20 |
| *Bacillus cereus* | 6.84 | 20.00 |
| *Escherichia colui* | 3.83 | 11.49 |
| *Pseudomonas aeruginosa* | 1.71 | 5.14 |

The composition is non toxic and is suitable for other applications, for example general antiseptic for wound cleaning and for sanitizing food such as eggs.

In the foregoing manner, an aqueous antiseptic composition for eliminating microorganisms that cause Bovine mastitis in dairy animals is disclosed. Although only an embodiment of the invention are disclosed, it becomes apparent to one skilled in the art in view of this disclosure that numerous changes and/or modifications can be made without departing from the scope and spirit of the invention.

The invention claimed is:

1. An antiseptic teat dip microemulsion composition for dairy animals comprising:
    10 to 50% by volume essential oil from Cymbopogan citratus (DO) Stapf (Gramineae);
    10 to 30% by weight of at least one solubilizing agent selected from at least one of polyethylene glycol 1000 monocetyl ether, polyoxethylene monolaurate, polyxyethylene, monolaurate, sodium lauryl sulfate, sodium-2-ethyhexyl sulfosuccinate and simethyl amine oxide;
    10 to 30% by volume of a carrier oil, selected from at least one of mineral oil, isopropyl myristate oil, isopropyl palmitate oil, palm oil (*Elaeis guineensis*), sunflower oil (*Helianthus annus*), olive oil (*Olea europaea*), coconut oil (*Cocos nucifera*), sesame oil (*Sesamum idicum*) and soya bean oil (*Glycine max*); and
    an organic acid for adjusting the pH level of the composition to between 3 and 6;
    wherein application of the composition effectively eliminates mastitis-causing microorganisms consisting of one or a combination of *Staphylcoccus aureus, Streptococcus agalactiae, Bacillus cereus, Escherichia coli*, and *Pseudomonas aeruginosa*.

2. The composition of claim 1, wherein carrier oil provides an emollient in 10 to 25% by volume of the total composition.

3. The composition of claim 1, wherein the solubilizing agent comprises polyethylene glycol 1000 monocetyl ether and sodium lauryl sulfate in a ratio by weight of 1:2.

4. The composition of claim 1, wherein the organic acid is selected from at least one of acetic acid, citric acid and tartaric acid.

5. The composition of claim 1 further comprising an electrolyte of 0.5 to 2% by weight of composition.

6. The composition of claim 1, further comprising an electrolyte selected from at least one of sodium chloride and sodium citrate.

7. The composition of claim 1, wherein the composition possesses anti-microbial activity against both coliform and non-coliform microorganisms.

8. The composition of claim 7, wherein the time taken for a 1-log reduction in the amount of microorganisms after exposure to the composition is between approximately 1 and 7 seconds.

9. The composition of claim 7, wherein the time taken for a 3-log reduction in the amount of microorganisms after exposure to the composition is between approximately 4 and 20 seconds.

* * * * *